United States Patent [19]

Foote et al.

[11] Patent Number: 5,770,391
[45] Date of Patent: Jun. 23, 1998

[54] REAGENTS AND METHODS FOR USE IN BIOLUMINESCENCE

[75] Inventors: Nicholas Peter Martin Foote, Cambridge; Peter Leonard Grant, Cambs., both of United Kingdom

[73] Assignee: Celsis International PLC, Cambridge, United Kingdom

[21] Appl. No.: 564,083

[22] PCT Filed: May 27, 1994

[86] PCT No.: PCT/GB94/01163

§ 371 Date: Nov. 30, 1995

§ 102(e) Date: Nov. 30, 1995

[87] PCT Pub. No.: WO94/28169

PCT Pub. Date: Dec. 8, 1994

[30] Foreign Application Priority Data

Jun. 1, 1993 [GB] United Kingdom .................... 9311241

[51] Int. Cl.⁶ ..................................................... C12Q 1/66
[52] U.S. Cl. ........................ 435/8; 435/4; 435/8; 435/15; 435/16; 435/18; 435/19; 435/21; 435/25; 435/26; 435/28; 436/501
[58] Field of Search .............................. 435/6, 7.1, 8–26, 435/810, 4, 28; 436/501

[56] References Cited

FOREIGN PATENT DOCUMENTS 0238352 9/1987 European Pat. Off. .
0441469 8/1991 European Pat. Off. .

OTHER PUBLICATIONS

*Biochemistry* (by A. L. Lehninger, Publ. by Worth Publishers, Inc., New York, N.Y., 1970) p. 390.
*Principles of Biochemistry* (by White et al., Publ. by McGraw–Hill Co., New York, N.Y., 1973) pp. 729–730 and 482.
Traverso–Cori et al. (1970) Archives of Biochemistry and Biophysics, vol. 137, pp. 133–142.
Robinson et al. (1986) Archives of Biochemistry and Biophysics, vol. 248, No. 2, pp. 502–515.
Jakubowski, H., A. Guranowski (1983) "Enzymes Hydrolyzing ApppA and/or AppppA in Higher Plants" The Journal of Biological Chemistry 258(16):9982–9989.
Sillero, M.A.G. et al. (1991) "Synthesis of dinucleoside polyphosphates catalyzed by firefly luciferase" Eur. J. Biochem. 202:507–513.

*Primary Examiner*—Ardin H. Marschel
*Attorney, Agent, or Firm*—Saliwanchik, Lloyd & Saliwanchik

[57] ABSTRACT

The subject invention pertains to a combination of enzyme activities comprising an ATP-degrading enzyme and one or more enzymes capable of degrading substances, other than ATP, that are substrates for the light-emitting reaction of firefly luciferase. These activities can be used to treat a growth medium in order to reduce background to negligible amounts, in a subsequent bioluminescence assay.

13 Claims, No Drawings

REAGENTS AND METHODS FOR USE IN BIOLUMINESCENCE

This application is a 371 filing of PCT/GB94/01163, filed May 27, 1994.

FIELD OF THE INVENTION

This invention relates to reagents for use in bioluminescence, and to their use.

BACKGROUND OF THE INVENTION

The background level of bioluminescence signal is often a problem when using the firefly luciferase reaction to measure adenosine 5'-triphosphate (ATP) levels deriving from prokaryotic cells, eukaryotic cells or both. Particular problems occur when the sample contains growth medium from a natural source, which is often the case in microbiological assays. Since such media are produced from living material, they tend to contain a significant amount of ATP. Most of the background bioluminescence signal arising from them can be removed by reaction with an ATPase enzyme such as potato apyrase or an ATP-utilising enzyme such as a kinase together with its co-substrate. However, a proportion of the signal always remains and can interfere with sensitive bioluminescence measurements. The source has always been thought of as non-microbial or non-cellular ATP which is somehow unavailable to ATPase enzymes, perhaps by reason of being sequestered.

SUMMARY OF THE INVENTION

The present invention is based on the discovery that the residual background bioluminescence signal can be removed by reaction with certain other enzymes such as phosphodiesterase I from snake venom (E.C. 3.1.4.1; Enzyme Nomenclature 1984, Academic Press), acid phosphatase (E.C. 3.1.3.2) and alkaline phosphatase (E.C. 3.1.3.1). Likely candidates for this "non-degradable ATP" are substances structurally related to ATP that are not attacked by apyrase, or by other enzymes which have ATP as a substrate, yet give rise to light when acted upon by firefly luciferase. They may be true substrates of luciferase, or be acted upon by luciferase to form a true substrate such as ATP, or may break down to form ATP or another luciferase substrate by other unidentified means.

Flavine adenine dinucleotide (FAD) has been identified as one such substance. It occurs in many microbiological growth media and biological samples, is structurally related to ATP, appears to act as a light-emitting substrate for firefly luciferase, but is not degraded by apyrase; it is destroyed by snake venom phosphodiesterase I. Other such substances are adenosine 5'-tetraphosphate ($p_4A$) and other adenosine polyphosphates, diadenosine 5',5'''-$P^1$,$P^4$-tetraphosphate ($Ap_4A$) and other diadenosine polyphosphates, and other dinucleoside polyphosphates such as $Gp_4A$ and $Gp_5A$. It is likely that other, as yet unidentified, derivatives of ATP will have similar properties. A few of these have previously been suggested to act as low-efficiency light-emitting luciferase substrates; see Momsen (1978) Biochm. Biophys. Res. Commun. 84:816–822, and Sillero et al (1991) Eur. J. Biochem. 202:507–513.

These compounds mentioned may be destroyed by suitable enzymatic activity, e.g. snake venom phosphodiesterase I or phosphatases. Other enzymes exist which will act upon these nucleotide derivatives with various degrees of specificity. For example, adenosine tetraphosphatase (E.C. 3.6.1.14) can be used in the method of the invention: it hydrolyses the luciferase substrate adenosine 5'-tetraphosphate to give ATP, which will subsequently be destroyed by apyrase. Diadenosine 5',5'''-$P^1$,$P^4$-tetraphosphatase (E.C. 3.6.1.17), which has been isolated from yellow lupin seeds (Jakubowski et al (1983) J. Biol. Chem. 258 (16):9982–9989), also produces ATP from its substrates and could be used in combination with apyrase in cases where part of the residual bioluminescence signal arises from $Ap_4A$.

A reagent to treat liquids, in order to reduce their response in a bioluminescent ATP assay, therefore comprises a combination of an ATP-degrading enzyme, such as potato apyrase, and one or more enzymes that degrade non-ATP luciferase substrates, together with additional divalent metal ions, such as $Mg^{2+}$, if required. This combination of enzymes, or of enzyme activities in at least one material, can be used, for example, to treat a growth medium.

DESCRIPTION OF THE INVENTION

When the reagent of the invention is used with microbiological growth media, the broth is usually treated within a few hours of preparation so that significant microbial growth in the non-sterile solution does not occur. After the enzyme treatment, the broth can be sterilised as normal, e.g. by filtration or by autoclaving. Autoclaving or heat-treatment will have the effect of destroying the enzyme activities, so high levels of the enzymes can be used yet will not interfere with subsequent assays.

Alternatively, the broth and enzymes can be sterile-filtered after being mixed together, which will not destroy the activities. On the one hand, when using a sterile mixture, it is possible to use long treatment times and low enzyme levels to ensure that the added enzymes have a negligible effect on subsequent ATP assays. On the other hand, higher levels of active enzymes may be advantageous in microbial enrichment assays where a sample is added to the treated broth and incubated before assay by bioluminescence, since free ATP, FAD or other luciferase substrate which might be present in the sample will be removed during the incubation step.

When a sample is to be assayed without the enrichment step, and the sample matrix gives rise to a significant background signal (for instance most foods and drinks, or swabs with food or drink residues), the enzyme reagent can be added beforehand to reduce the background in a similar way to above. Microbial and/or cellular ATP subsequently released can then be directly measured without background interference.

The following Examples illustrate the invention and should not be construed as limiting.

EXAMPLE 1

To 250 ml of freshly-prepared Nutrient Broth No. 2 (oxoid) was added potato apyrase and snake venom phosphodiesterase I to give final activities of 2 and 0.2 International Units per liter respectively. The mixture was then filtered through a 0.22 $\mu$m membrane filter into a sterile vessel and incubated at 25° C. for 16 hours.

The response in the firefly luciferase reaction was measured before and after treatment using HS (High Sensitivity) Luciferase-Luciferin Reagent (Celsis) and a Berthold Biolumat luminometer. Before treatment, the response corresponded to 550 pM ATP; after treatment, it corresponded to less than 0.03 pM ATP.

EXAMPLE 2

Nutrient Broth No. 2 (Oxoid) from a different batch was prepared using sterile water. Portions were put aside and either apyrase alone (10 I.U./liter) or apyrase (10 I.U./liter) plus snake venom phosphodiesterase I (1 I.U./liter) were added, but this time the mixture was not sterilised. After 1 hour at room temperature, the response in the luciferase assay was recorded as in Example 1. The results were as follows:

| Sample | Equivalent [ATP] (pM) |
| --- | --- |
| Untreated Nutrient Broth | 1490 |
| + apyrase, 1 hour | 8.6 |
| + apyrase + PDE I, 1 hour | 1.2 |

EXAMPLE 3

Sabouraud liquid medium (Oxoid), prepared with sterile water, was treated at room temperature with various commercial grades of potato apyrase (0.25 I.U./ml) with and without acid phosphatase from sweet potato (0.25 I.U./ml). After two hours, the apparent ATP content was measured by bioluminescence, with the following results:

| | Equivalent [ATP] (pM) | |
| --- | --- | --- |
| Sample | −phosphatase | +phosphatase |
| Untreated broth | 9722 | N/D |
| Apyrase Grade I | 51 | 23 |
| Apyrase Grade III | 57 | 24 |
| Apyrase Grade V | 233 | 24 |
| Apyrase Grade VII | 98 | 23 |

The amount of apyrase present was enough to reduce the level of genuine ATP to below the limit of detection of the assay. The residual substance or substances giving rise to light emission in the assay were removed to varying extents by apyrase alone, and this may represent different levels of contaminant enzyme activities in the preparations. Addition of acid phosphatase reduced the bioluminescence signal further, to a consistent value.

EXAMPLE 4

Another batch of Sabouraud liquid medium was prepared with sterile water and divided into three samples. One had no additions; to another was added potato apyrase and sweet potato acid phosphatase (0.25 I.U./ml each); to the third was also added snake venom phosphodiesterase I (0.01 I.U./ml). The mixtures were then sterile-filtered and left at room temperature under sterile conditions for 24 hours, at which point they were assayed by bioluminescence. The results were as follows:

| Sample | Equivalent [ATP] (pM) |
| --- | --- |
| Untreated broth | 11060 |
| + apyrase + acid phosphatase | 18.4 |
| + apyrase + acid phosphatase + PDE I | 0.8 |

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A purified composition comprising an apyrase enzyme and one or more enzymes capable of degrading substances, other than ATP, wherein said substances are, or can undergo conversion to become, substrates utilized in the light-emitting forward reaction of firefly luciferase, wherein said one or more enzymes capable of degrading substance other than ATP do not include luciferase and wherein each of said one or more enzymes capable of degrading substances other than ATP reduce the light emission produced from said light-emitting reaction of firefly luciferase.

2. The composition of claim 1, in which a product of reaction of said one or more enzymes capable of degrading substances other than ATP with a non-ATP substrate is ATP.

3. The composition according to claim 1, in which said one or more enzymes capable of degrading substances other than ATP have FAD-degrading activity.

4. The composition according to claim 1, comprising an ATPase and an enzyme having phosphodiesterase I activity.

5. The composition according to claim 1, which comprises an ATPase and an enzyme having phosphatase activity.

6. The composition according to claim 1, in which ATPase is potato apyrase.

7. The composition according to claim 1, in freeze-dried form.

8. The composition according to claim 1, which additionally comprises $Mg^{2+}$ or other divalent metal ion.

9. The composition according to claim 1, which additionally comprises one or more bioluminescence reagents selected from the group consisting of luciferin and luciferase.

10. The composition according to claim 7, in which the components are provided in kit form, in two or more containers.

11. A method for treating a growth medium, which comprises adding to the medium the enzyme activities defined in claim 1.

12. A method for reducing the background bioluminescence in a bioluminescence assay which comprises the steps of adding to the sample an ATP-degrading enzyme and one or more enzymes capable of degrading substances, other than ATP, wherein said substances are, or can undergo conversion to become, substrates utilized in the light-emitting forward reaction of firefly luciferase, wherein said one or more enzymes capable of degrading substances other than ATP do not include luciferase and wherein each of said one or more enzymes capable of degrading substances other than ATP reduce the light emission produced from said light-emitting reaction of firefly luciferase, and subsequently assaying the sample for bioluminescent light emission.

13. The composition according to claim 8, in which the components are provided in kit form, in two or more containers.

* * * * *